(12) United States Patent
Diehl et al.

(10) Patent No.: US 9,545,439 B2
(45) Date of Patent: *Jan. 17, 2017

(54) EMULSION VACCINE COMPOSITIONS COMPRISING ANTIGEN AND ADJUVANT IN THE AQUEOUS PHASE

(71) Applicant: Zoetis Services LLC, Florham Park, NJ (US)

(72) Inventors: Evan James Diehl, Iowa City, IA (US); David Leon Lutz, Harcourt, IA (US); Jeffrey Harold Rodenberg, Kalamazoo, MI (US); Mahesh Kumar, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/618,628

(22) Filed: Feb. 10, 2015

(65) Prior Publication Data

US 2015/0297710 A1  Oct. 22, 2015

Related U.S. Application Data

(63) Continuation of application No. 12/142,160, filed on Jun. 19, 2008, now Pat. No. 8,980,288.

(60) Provisional application No. 60/936,571, filed on Jun. 20, 2007.

(51) Int. Cl.
| | | |
|---|---|---|
| A61K 39/12 | (2006.01) | |
| A61K 39/145 | (2006.01) | |
| A61K 45/00 | (2006.01) | |
| A61K 9/107 | (2006.01) | |
| C12N 7/00 | (2006.01) | |
| A61K 39/00 | (2006.01) | |
| A61K 39/39 | (2006.01) | |

(52) U.S. Cl.
CPC ............ *A61K 39/145* (2013.01); *A61K 9/107* (2013.01); *A61K 39/00* (2013.01); *A61K 39/12* (2013.01); *C12N 7/00* (2013.01); *A61K 39/39* (2013.01); *A61K 2039/552* (2013.01); *A61K 2039/55505* (2013.01); *A61K 2039/55511* (2013.01); *A61K 2039/55555* (2013.01); *A61K 2039/55561* (2013.01); *A61K 2039/55566* (2013.01); *A61K 2039/55572* (2013.01); *C12N 2760/16134* (2013.01); *C12N 2760/16171* (2013.01)

(58) Field of Classification Search
None
See application file for complete search history.

(56) References Cited

U.S. PATENT DOCUMENTS

| | | |
|---|---|---|
| 3,639,577 A | 2/1972 | Urton et al. |
| 5,026,546 A | 6/1991 | Hilgers et al. |
| 5,109,026 A | 4/1992 | Hoskinson et al. |
| 5,744,137 A | 4/1998 | Stone |
| 6,086,901 A | 7/2000 | O'Hagan et al. |
| 6,340,464 B1 | 1/2002 | Hilgers et al. |
| 6,585,978 B1 | 7/2003 | Montelaro et al. |
| 6,676,958 B2 | 1/2004 | Gerber |
| 7,018,638 B2 | 3/2006 | Chu et al. |
| 7,163,926 B1 | 1/2007 | Audonnet et al. |
| 7,169,394 B2 | 1/2007 | Chu et al. |
| 7,862,821 B2 | 1/2011 | Audonnet et al. |
| 2008/0003201 A1 | 1/2008 | Chu |

FOREIGN PATENT DOCUMENTS

WO  2004/058142  7/2004

OTHER PUBLICATIONS

PCT International Search Report, PCT/US2008/067433, mailed Sep. 22, 2008 (3 pages).
Hilgers et al., "Effect of various adjuvants on secondary immune response in chickens", Veterinary Immunology and Immunopathology, 66:159-171, 1998.

*Primary Examiner* — Stacy B Chen
(74) *Attorney, Agent, or Firm* — Vyacheslav Vasilyev

(57) ABSTRACT

Emulsion vaccine formulations containing an antigen and an adjuvant in the aqueous phase are used for the vaccination of animals wherein the adjuvant is an acrylic polymer and/or dimethyl dioctadecyl ammonium bromide (DDA). These formulations can be prepared by mixing an aqueous phase containing the antigen and adjuvant with an oil phase in the presence of an emulsifier.

6 Claims, 3 Drawing Sheets

EMULSION VACCINE COMPOSITIONS COMPRISING ANTIGEN AND ADJUVANT IN THE AQUEOUS PHASE

CROSS-REFERENCE TO RELATED APPLICATIONS

This application is a continuation of U.S. patent application Ser. No. 12/142,160 filed Jun. 19, 2008, issued as U.S. Pat. No. 8,980,288 on Mar. 17, 2015, which claims the benefit of priority to U.S. Provisional Application No. 60/936,571.

BACKGROUND OF THE INVENTION

Field of the Invention

The present invention relates to water-in-oil vaccine formulations, processes of making the formulations and the use of such formulations for the vaccination of animals.

Background Art

The cornerstone of many infectious disease control programs is induction of specific immunity by vaccination with either live or inactivated microorganisms or their products. An effective vaccination procedure allows the development of a state of immunologic memory in an animal for an antigen, which leads to a rapid and robust immunological response in the animal, upon subsequent contact with the antigen. Some antigens, however, are only weakly immunogenic. Such antigens may be unable to induce an immune response sufficient to provide an effective protection for the animal upon subsequent challenge, or may require administration with additional agents that boost immunogenicity to provide effective protection.

The immunogenicity of an antigen can be increased by administering it in a mixture with substances, called adjuvants, which increase the response against the antigen either by directly acting on the immune system or by modifying the pharmacokinetic characteristics of the antigen and thereby increasing the interaction time between the latter with the immune system.

Emulsions made from water and oil (e.g., water-in-oil, oil-in-water, water-in-oil-in-water emulsions) can be used as adjuvants in vaccines. Water-in-oil emulsions are commonly used as adjuvants in animal vaccines, e.g., in poultry vaccines. In general, to make a water-in-oil emulsion, an aqueous phase antigen is slowly added to a mineral oil carrier in the presence of one or more emulsifying agent(s), resulting in micelles consisting of oil droplets within which the aqueous antigen resides. It is believed that the oil component induces the migration of immune cells to the injection site, and also serves to protect the antigen and extend the period of time for the immune cells to process the antigen. The end result is an enhancement of the immune response as compared to simply injecting the antigen by itself.

Adjuvants consisting of acrylic polymers are sometimes used as alternatives to oil-based emulsions in vaccine formulations. An exemplary acrylic polymer is a water-soluble polymer of acrylic acid crosslinked with polyallyl sucrose which is also known as Carbopol. U.S. Pat. No. 5,026,546, for example, refers to the use of dimethyl dioctadecyl ammonium bromide (DDA) as a vaccine adjuvant and the addition of Carbopol to improve the solubility of DDA in water.

Both oil-based emulsions and acrylic polymers have distinct advantages when used as adjuvants in vaccine formulations. Combining water-in-oil emulsions and acrylic polymers, however, would have been discouraged since it is expected that acrylic polymers such as Carbopol would be highly reactive in association with an oil emulsion. For example, U.S. Pat. No. 5,026,546, discussed above, mentions the use of Carbopol but provides no suggestion of using DDA and/or Carbopol in water-in-oil or oil-in-water emulsions. In addition, with regard to adjuvants for certain species such as poultry, acrylic polymers have been avoided due to their perceived high reactivity in general. Thus, there exists a need in the art for novel adjuvants which provide the combined advantages of acrylic polymers and water-in-oil emulsions without the drawbacks of adverse reactivity caused by the acrylic polymers in the vaccinated animal.

BRIEF SUMMARY OF THE INVENTION

The present invention is based, in part, on the surprising discovery that formulating oil-based emulsion vaccine compositions with an acrylic polymer such as Carbopol in the aqueous phase significantly increases the immune response generated by the vaccine composition as compared to oil-based emulsion vaccine compositions that do not include an acrylic polymer. Moreover, by formulating an acrylic polymer in the aqueous phase of a water-in-oil emulsion, the expected adverse reactivity of the acrylic polymer in the animal was avoided.

Thus, the present invention provides vaccine compositions comprising water-in-oil emulsions. The water-in-oil emulsions of the invention comprise an oil component and an aqueous component. The aqueous component comprises at least one antigen and at least one adjuvant selected from the group consisting of an acrylic polymer and dimethyl dioctadecyl ammonium bromide (DDA). The present invention also includes methods of vaccinating an animal, said methods comprising administering to an animal a vaccine composition of the invention.

Other aspects of the invention include methods for making vaccine compositions that comprise water-in-oil emulsions. The methods of the invention comprise emulsifying an oil component with an aqueous component, wherein the aqueous component comprises at least one antigen and at least one adjuvant selected from the group consisting of an acrylic polymer and dimethyl dioctadecyl Ammonium bromide (DDA).

The above features and many other attendant advantages of the invention will become better understood by reference to the following detailed description when taken in conjunction with the accompanying drawings.

DETAILED DESCRIPTION OF THE INVENTION

Figure 1:
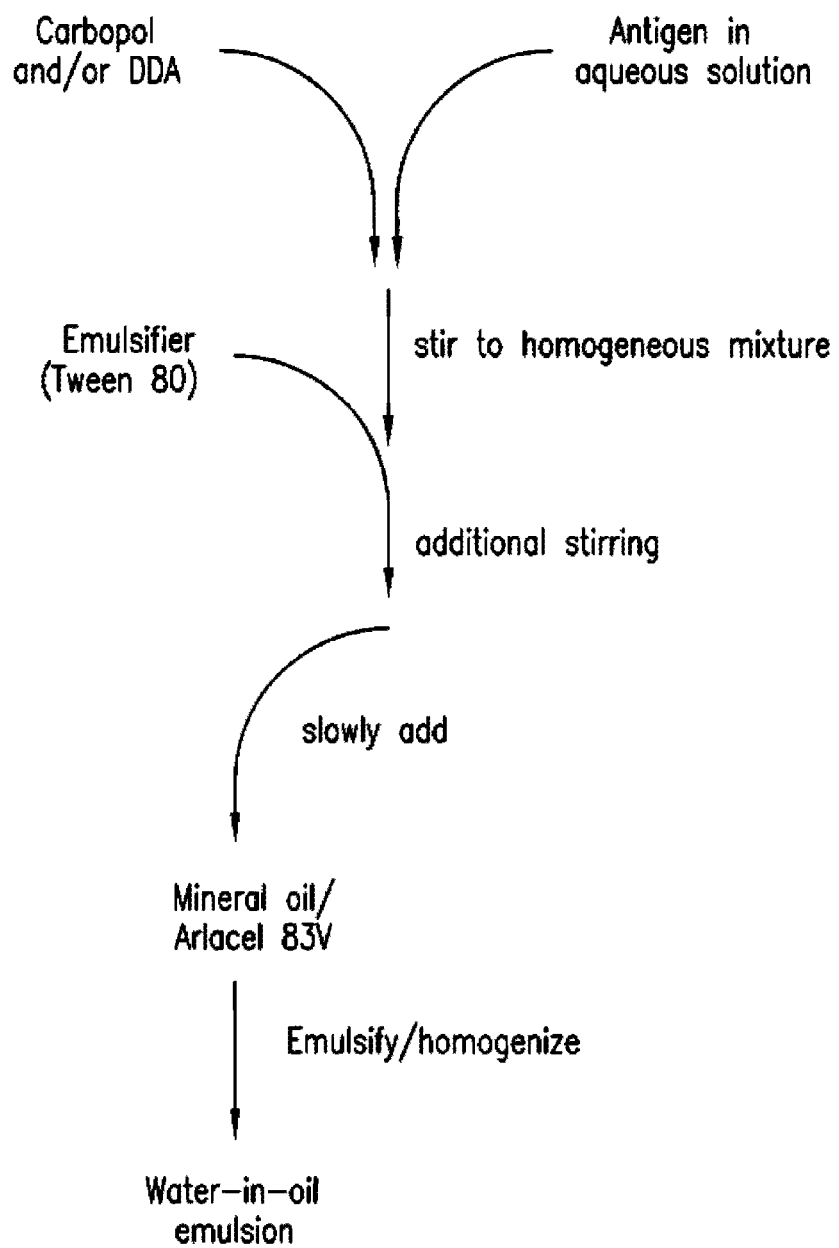
FIG. 1 is a flowchart showing an exemplary method for making an emulsion vaccine composition of the present invention.

The present invention provides vaccine compositions comprising an emulsion. The emulsion comprises an oil component and an aqueous component. The aqueous component comprises at least one antigen and at least one adjuvant. The adjuvant may comprise an acrylic polymer and/or DDA.

Emulsions

Different types of emulsions used in vaccine preparations include water-in-oil, oil-in-water, and water-in-oil-in-water emulsions. A preferred type of emulsion for use in the context of the present invention is a water-in-oil emulsion. A water-in-oil emulsion can further include one or more oil soluble surfactants, one or more water soluble surfactants, additional adjuvants, additional aqueous phase components, emulsion stabilizers, or combinations thereof. Methods for making water-in-oil emulsions are known in the art and are described elsewhere herein.

Vaccine Compositions

As used herein, a "vaccine composition" is a composition that can be used to elicit protective immunity in a recipient. Thus, after a subject has been vaccinated with an antigen, a vaccine prevents, delays, or lessens the severity of the development of a disease in the subject exposed to the same or a related antigen relative to a non-vaccinated subject. Protective immunity provided by a vaccine can be humoral (antibody-mediated) immunity or cellular immunity, or both. Vaccination may, e.g., eliminate or reduce the load of a pathogen or infected cells, or produce any other measurable alleviation of an infection. Vaccination may also reduce a tumor burden in an immunized (vaccinated) subject.

The term "protective immunity" as used herein refers to immunity acquired against an antigen when a subject has been exposed to the antigen resulting in an immune response (either active/acquired or passive/innate, or both) in the subject which leads to inactivation and/or reduction in the load of the antigen and the creation of immunological memory (e.g., memory T- or B-cells).

Protective immunity provided by vaccination may be partial or provided in only a fraction of vaccinated subjects. Thus, a vaccine may elicit protective immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs, e.g., to prevent organ rejection or suppress an autoimmune condition). Vaccines that provide protection to a portion of the immunized population are nevertheless useful and are considered effective.

Adjuvants

The term "adjuvant" as used herein refers to a compound that enhances a subject's immune response to an antigen when administered conjointly with that antigen.

Adjuvant-mediated enhancement of the immune response can be assessed by any method known in the art, including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; (iii) an increase in the level of one or more Type I cytokines; and (iv) in vivo protection after live challenge.

An immune response is believed to be enhanced, if any measurable parameter of antigen-specific immunoreactivity (e.g., antibody titer or T cell production) is increased at least 10% when a subject is challenged with an antigen and adjuvant compared to a subject challenged with the antigen alone. In certain embodiments of the present invention, an immune response is enhanced if any measurable parameter of antigen-specific immunoreactivity is increased by at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, at least 95%, at least 100%, at least 125%, at least 150%, at least 175%, at least 200%, at least 225%, at least 250%, at least 275%, at least 300%, at least 350%, at least 400%, at least 450%, at least 500%, or at least 1000%.

The adjuvant is preferably an acrylic polymer, dimethyl dioctadecyl ammonium bromide (DDA), or a combination of an acrylic polymer and DDA. The adjuvant is preferably a water soluble or water dispersible adjuvant.

An acrylic polymer, as used herein, is any polymer or copolymer that contains an acrylic moiety. Exemplary acrylic polymers include, e.g., polyacrylic acid, methacrylic acid, methacrylate, acrylamide, acrylate, acrylnitrile, and alkyl-esters of polyacrylic acid. Examples of acrylic copolymers include, e.g., poly (acrylamide-co butyl, methacrylate), acrylic-methacrylic acid, acrylic-acrylamide and poly (methacrylate). Examples of commercially available acrylic polymers include, Carbopol (B. F. Goodrich Co., Cleveland, Ohio), Carboset, (B. F. Goodrich Co., Cleveland, Ohio), Neocryl (Avecia, Inc., Wilmington, Del.), and Eudragit (Rohm Tech, Inc., Malden, Mass.). A particularly useful acrylic polymer for use in the emulsions of the present invention is Carbopol, which is also referred to, and known in the art, generically as a water-soluble polymer of acrylic acid crosslinked with polyallyl sucrose.

Specific acrylic polymers that may be included in the aqueous phase of the water-in-oil emulsions of the present invention include alkyl-polyacrylic acid ("alkyl-PAA") polymers, as described in U.S. Pat. No. 6,340,464, and references cited therein. Exemplary alkyl-PAA polymers include decyl-PAA (C10-PAA), octyl-PAA (C8-PAA), butyl-PAA (C4-PAA), and methyl-PAA (C1-PAA). (See, e.g., U.S. Pat. No. 6,340,464, Table I). Octyl-PAA may alternatively be referred to as "octyl-alkyl-PAA" or "OA-PAA."

In certain embodiments of the invention, the aqueous component also comprises lecithin. In the context of the present invention, the lecithin can be any lecithin, for instance, lecithin lipoidal material, such as phosphotidylcholine, that can be used to form liposomes. Phospholipids, lysophospholipids, glycolipids and neutral lipids comprise the typical composition of lecithin. Lecithins are molecules that, when completely hydrolyzed, yield two molecules of fatty acid, and one molecule each of glycerol, phosphoric acid, and a basic nitrogenous compound, which is usually choline. The fatty acids obtained from lecithins on hydrolysis are usually, but not limited to, oleic, palmitic, and stearic acids. The phosphoric acid may be attached to the glycerol in either an α- or the β-position, forming α-glycerophosphoric acid or β-glycerophosphoric acid, respectively, and producing the corresponding series of lecithins which are known as α- and β-lecithins. Examples of adjuvants comprising lecithin and an acrylic polymer are described in, e.g., U.S. Pat. No. 6,676,958.

In the vaccine compositions of the present invention, the acrylic polymer and/or DDA may be used in conjunction with one or more additional adjuvants. Exemplary additional adjuvants include, but are not limited to, complete Freund's adjuvant, incomplete Freund's adjuvant, MF59, or SAF; mineral gels such as aluminum hydroxide (alum, for example, $Al(OH)_3$ reHydragel® available from Reheis, Berkley Heights, N.J.)), aluminum salts (e.g., aluminum phosphate) or calcium salts (e.g., calcium phosphate); microbially-derived adjuvants such as cholera toxin (CT), pertussis toxin, *Escherichia coli* heat-labile toxin (LT), mutant toxins (e.g., LTK63 or LTR72), *Bacille* Calmette-Guerin (BCG), lipopolysaccharides (LPS), mycobacteria, tetanus toxin, *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers or surfactants, muramyl peptide analogues (e.g., N-acetyl-muramyl-L-threonyl-D-isoglutamine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, synthetic polynucleotides, surface active substances such as lysolecithin, pluronic polyols, polyanions, peptides, hydrocarbon emulsions, or keyhole limpet hemocyanins (KLH). Additional adjuvants include CMC (carboxyl methylcellulose) and HPMC (hydroxypropyl methylcellulose).

As illustrated in the Examples provided herein, the use of adjuvants, such as Carbopol, alkyl-PAA (e.g., OA-PAA) and/or DDA, in the aqueous phase of water-in-oil emulsion vaccines surprisingly improved the antigenicity of the vaccines as compared to traditional water-in-oil emulsion vaccines without adjuvants.

Antigens

The term "antigen" as used herein refers to an agent that when introduced into a subject, is recognized by the immune system of the host and is capable of eliciting an immune response and generating protective immunity. Antigens include without limitation, "surface antigens" that are expressed naturally on the surface of a pathogen, or the surface of an infected cell, or the surface of a tumor cell.

In certain embodiments of the invention, the antigen is an infectious agent. The infectious agent may be a live infectious agent or it may be a killed or inactivated infectious agent. Exemplary infectious agents that can serve as antigens in the vaccine compositions of the present invention include, e.g., viruses, bacteria, fungi, parasites or other microorganisms. The antigen can also be a component or product derived from a virus, bacterium, fungus, parasite or other microorganism. Alternatively, the antigen may be a product obtained by chemical synthesis, protein, polypeptide, peptide, polysaccharide, glycoprotein, glycolipid, nucleic acid, or combination thereof. One of ordinary skill in the art will understand that when nucleic acid antigens are introduced into an animal, they will ultimately lead to production of, e.g., a peptide or protein, which will in turn elicit an immune response.

When administered to a subject, antigens specifically interact with an antigen recognition molecule of the immune system, such as, e.g., an immunoglobulin (antibody) or T cell antigen receptor (TCR) to elicit an immune response leading to the formation of memory cells (e.g., memory B- and T-cells) and protective immunity. Some antigens require co-administration with an adjuvant or carrier to illicit an immune response.

A vaccine can contain a component (e.g., a vector) that produces an antigen in addition to or in place of an antigen. The terms "vector", "cloning vector", and "expression vector" mean the vehicle by which a nucleic acid sequence (e.g., a foreign gene) can be introduced into a host cell, so as to transform the host and promote expression (e.g., transcription and/or translation) of the introduced sequence of an antigen. Vectors include plasmids, phages, and viruses (e.g., a RNA virus such as retroviruses and lentiviruses).

In certain embodiments of the present invention where the antigen is an infectious agent, the infectious agent may be an agent that is capable of infecting an animal. For example, the infectious agent may be capable of infecting a human, avian (e.g., chicken, turkey, duck, pigeon, etc.), canine, feline, bovine, porcine, or equine animal.

Non-limiting examples of disease pathogens and/or conditions for which antigens can elicit protective immunity are influenza virus, Newcastle disease virus, infectious bronchitis virus, rhinovirus, parainfluenza virus, parvovirus (e.g., duck parvovirus), adenovirus, *Actinobaccilus pleuropneumoniae, Pasteurella multocida, Streptococcus pneumonia, Streptococcus pyogenes*, avian leukosis, infectious bursal disease, reovirus, pox, laryngotracheitis, Marek's disease, tetanus, hepatitis B, malaria, pneumococcal pneumonia, rotavirus, parvovirus, caronavirus, *E. coli, Salmonella, Shigella, Yersinia, Campylobactor, Clostridium, Vibrio* and *Giardia, Entamoeba*, and *Cryptosporidium*. Antigens can also elicit protective immunity against a malignancy (e.g., solid or blood tumors such as sarcomas, carcinomas, gliomas, blastomas, pancreatic cancer, breast cancer, ovarian cancer, prostate cancer, lymphoma, leukemia, and melanoma).

In certain embodiments, the antigen is an influenza virus, e.g., an inactivated influenza virus. The inactivated influenza virus may be obtained by traditional methods or by so-called "reverse genetics" techniques. Exemplary reverse genetics methods that can be used to make influenza virus antigens for use in the vaccine compositions of the present invention are disclosed, e.g., in U.S. Pat. Nos. 6,951,754, 5,578,473, 5,820,871, 6,887,699, 6,544,785, and in U.S. Patent Appl. Publication Nos. 2003/0035814, 2006/0134138, 2006/0057116, 2005/0037487, 2005/0003349, 2006/0166321, and 2004/0142003. The contents of the aforementioned patents and patent application publications are incorporated by reference herein in their entireties.

Any inactivated influenza viruses can be used in the context of the present invention including any inactivated influenza A strain (e.g., avian influenza strain). The influenza viruses may be recombinant influenza viruses produced by traditional egg-based methods or by reverse genetics techniques mentioned hereinabove. The recombinant viruses may possess any combination of hemagglutinin (HA) and neuraminidase (NA) subtypes. Exemplary inactivated influenza virus that can be used as an antigen in the context of the present invention include viruses with an H1, H5, H7 or H9 hemagglutinin combined with any of N1, N2, N3, N4, N5, N6, N7, N8 or N9. In general, the hemagglutinin subtype of the antigen is chosen on the basis of the hemagglutinin subtype(s) exhibited by circulating infectious influenza strains.

When the antigen is an inactivated influenza virus such as, e.g., H5N3 or H5N9, the amount of antigen in the vaccine composition is typically expressed in terms of hemagglutination units (HAU) per dose. For instance, in certain embodiments of the invention, the antigen is an inactivated influenza virus and is present in the vaccine composition in an amount of 50 to 1000 HAU per dose. In particular embodiments, each dose of vaccine composition contains about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, about 500, about 505, about 510, about 515, about 520, about 2525, about 530, about 535, about 540, about 545, about 550, about 555, about 560, about 565, about 570, about 575, about 580, about 585, about 590, about 595, about 600, about 605, about 610, about 615, about 620, about 625, about 630, about 635, about 640, about 645, about 650, about 655, about 660, about 665, about 670, about 675, about 680, about 685, about 690, about 695, about 700, about 705, about 710, about 715, about 720, about 725, about 730, about 735, about 740, about 745, about 750, about 755, about 760, about 765, about 770, about 775, about 780, about 785, about 790, about 795, about 800, about 805, about 810, about 815, about 820, about 825, about 830, about 835, about 840, about 845, about 850, about 855, about 860, about 865, about 870, about 875, about 880, about 885, about 890, about 895, about 900, about 905, about 910, about 915, about 920, about 925, about 930, about 935, about 940, about 945, about 950, about 955, about 960, about 965, about 970, about 975, about 980, about 985, about 990, about 995, or about 1000 HAU.

In certain other embodiments, each dose of vaccine composition contains about 182 HAU, 256 HAU or 512 HAU.

Oil Component

The vaccine compositions of the present invention also include an oil component. Examples of oils that can be included in the oil component include without limitation terpene oils such as squalane and squalene; vegetable oils such as soybean oil, olive oil, corn oil, jojoba oil, peanut oil, cottonseed oil, sunflower oil, safflower oil, sesame oil, apricot oil, avocado oil, wheat germ oil, canola oil, linseed oil, and almond oil; fish oils such as shark oil, orange roughy oil, Menhaden oil, and cod liver oil; animal oils such as mink oil, lard oil, and chicken fat oil; and synthetic oils such as ethyl oleate, isopropyl myristate, Migiyoi® 840 (Sasol North America inc., Houston, Tex.), and Captex® 300 (Abitec Corp., Columbus, Ohio) as well as mineral oil (available from Sigma-Aldrich, St. Louis, Mo.), triglyceride oil, propylene glycol derivatives, and pristane. The preferred oil of the oil phase is mineral oil. Combinations of these oils may also be used.

Additional Components

In certain embodiments of the present invention, the vaccine compositions may include one or more additional components such as, e.g., surfactants, buffers and stabilizing compounds.

Oil soluble surfactants include Arlacel® 83 (sorbitan sesquioleate, available from Uniquema, New Castle, Del.), Arlacel® A (mannide monooleate, available from Uniquema, New Castle, Del.), Arlacel® 80 (available from Uniquema, New Castle, Del.), Span® 80 (sorbitane monooleate, Sigma-Aldrich, St. Louis, Mo.), L121 poloxamer 401 (Pluronic® L121, BASF Corp., Florham Park, N.J.). One preferred oil soluble surfactant is Arlacel® 83.

Water soluble surfactants include Tween 80 (polyoxyethylene sorbitan monooleate, Sigma-Aldrich, St. Louis, Mo.). One preferred water soluble surfactant is Tween®80.

Aqueous phases can include a pH buffering component such as PBS (phosphate buffered saline), preservatives (e.g., methyl or propyl-p-hydroxybenzoates or sorbic acid), flavoring, coloring and sweetening agents.

Emulsions may be stabilized by inclusion of one or more stabilizers compounds. Classes of stabilizers include polymeric stabilizers and low molecular weight stabilizers. Polymeric stabilizers form gels in the bulk phases or other structures at interfaces and increase the viscosity of one or more of the phases or interfaces. Polymeric stabilizers include without limitation, proteins, starches, gums, cellulosics, polyvinyl alcohols, polyacrylic acid and polyvinyl pyrrolidone. These materials bind to the interface by covalent bonds or by electrostatic and hydrophobic interactions. They form an "interfacial complex" which is defined as an association of two or more surface active molecules at an interface in a relationship that does not exist in either of the bulk phases. Examples of low molecular weight stabilizers are, without limitation, cholesterol and fatty acid salts of divalent cations such as aluminum stearate.

Methods of Making the Vaccine Compositions of the Invention

The present invention also includes methods for making vaccine compositions. In one embodiment, the methods of the invention comprise emulsifying an oil component with an aqueous component. As described in more detail above, the aqueous component of the vaccine composition comprises at least one antigen and at least one adjuvant selected from the group consisting of an acrylic polymer and DDA. Any of the oil components, antigens, adjuvants and variations thereof that are described elsewhere herein can be used in the methods of the present invention.

In a particular embodiment, a method for making a vaccine composition is provided, wherein the method comprises: (a) combining an aqueous solution of an antigen with at least one adjuvant selected from the group consisting of an acrylic polymer and DDA to form an antigen/adjuvant mixture; (b) combining the antigen/adjuvant mixture of (a) with an oil component and an emulsifier to form an antigen/adjuvant/oil component mixture; and (c) emulsifying the antigen/adjuvant/oil component mixture of (b) to form a water-in-oil emulsion, thereby forming a vaccine composition.

The methods of the invention comprise emulsifying an oil component with an aqueous component to form, e.g., a water-in-oil (WO) emulsion. Methods for preparing water-in-oil emulsions for vaccine compositions are well known in the art. See, e.g., U.S. Pat. Nos. 5,109,026 and 5,744,137. in general, an aqueous phase (optionally including a surfactant) and an oil phase (optionally including a surfactant) are prepared and mixed to form a water-in-oil emulsion.

For example, water-in-oil emulsions of Carbopol or Carbopol+DDA may be prepared as follows: An aqueous phase is prepared by mixing one or more antigens and, optionally, Carbopol® or Carbopol®+DDA sequentially or simultaneously in an aqueous solution to form a homogenous mixture. A water soluble surfactant may optionally be mixed with the antigen-containing aqueous mixture. Additional aqueous components including additional adjuvants can be added to the aqueous phase. A flowchart illustrating one exemplary method for preparing a vaccine formulation of the invention is set forth in FIG. 1.

The total volume of each dose of vaccine composition can be, e.g., from 0.05 mL to 2.0 mL. For example, in certain embodiments, the volume of the dose of the vaccine composition is about 0.05 mL, about 0.10 mL, about 0.15 mL, about 0.20 mL, about 0.25 mL, about 0.30 mL, about 0.35 mL, about 0.40 mL, about 0.45 mL, about 0.50 mL, about 0.55 mL, about 0.60 mL, about 0.65 mL, about 0.70 mL, about 0.75 mL, about 0.80 mL, about 0.85 mL, about 0.90 mL, about 0.95 mL, or about 1.0 mL.

In preparing the vaccine compositions of the present invention, various proportions of aqueous component (e.g., the antigen in aqueous solution combined with adjuvant) to oil component can be used, as set forth in the following Table 1:

TABLE 1

| Aqueous Component | Oil Component |
|---|---|
| 5% | 95% |
| 10% | 90% |
| 15% | 85% |
| 20% | 80% |
| 25% | 75% |
| 30% | 70% |
| 35% | 65% |
| 40% | 60% |
| 45% | 55% |
| 50% | 50% |
| 55% | 45% |
| 60% | 40% |
| 65% | 35% |
| 70% | 30% |
| 75% | 25% |
| 80% | 20% |
| 85% | 15% |
| 90% | 10% |
| 95% | 5% |

One way to prepare a water-in-oil emulsion is to add the aqueous phase to the oil phase. This mixture is then manually shaken for 15 to 20 seconds, emulsified for 20 seconds using a high-shear probe (Brinkman homogenizer, Brinkman Instruments, Westbury, N.Y.) Polytron 10/35, vortexed, or similarly mixed using a technique familiar to those skilled in the art.

For industrial preparation of the surfactant composition-containing water-in-oil emulsion vaccines, the oil and surfactant-containing aqaqueous phases may be mixed with a Silverson homogenizer.

Those skilled in the art can appreciate that the relative quantities of the aqueous phase containing the antigen, the oil phase, and the surfactants can be adjusted to achieve emulsions with specific desired properties of viscosity.

Methods of Vaccinating an Animal

The present invention also includes methods of vaccinating an animal. The methods of the invention comprise administering to an animal any of the vaccine compositions described elsewhere herein.

The vaccine compositions of the invention can be administered to any animal, including, e.g., human, avian, canine, feline, bovine, porcine or equine animals. Exemplary avian animals include, e.g., avian animals, whether domestic or wild, and particularly to those which are commercially reared for meat or egg production. Without limitation thereto, exemplary avians include chickens, turkeys, geese, ducks, pheasants, and the like.

Vaccine formulations can be administered by, without limitation, transdermal delivery, or by transmucosal administration, including but not limited to, oral, buccal, intranasal, opthalmic, vaginal, rectal, intracerebral, intradermal, intramuscular, intraperitoneal, intravenous, subcutaneous routes, via scarification (scratching through the top layers of skin, e.g., using a bifurcated needle), by inhalation (pulmonary) or insufflation (either through the mouth or the nose), or by administration to antigen presenting cells, such as dendritic cells (DC), ex vivo followed by administration of the cells to the subject, or by any other standard route of immunization.

Preferably, the vaccine compositions of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Compositions of the present invention can also be formulated in rectal compositions such as suppositories or retention enemas.

According to the methods of the present invention, the vaccine compositions described herein are administered to a subject at therapeutically effective doses, preferably, with minimal toxicity.

The term "therapeutically effective" applied to the terms dose or amount refers to a quantity of a compound or pharmaceutical composition or vaccine that is sufficient to result in a desired activity upon administration to an animal in need of the compound, pharmaceutical composition or vaccine. As used herein with respect to adjuvant- and antigen-containing compositions or vaccines, the term "therapeutically effective amount/dose" is used interchangeably with the term "immunogenically effective amount/dose" and refers to the amount/dose of a compound (e.g., an antigen and/or an adjuvant) or pharmaceutical composition or vaccine that is sufficient to produce an effective immune response upon administration to an animal.

The phrase "pharmaceutically acceptable," refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

A therapeutically effective dose can be determined from dose-response curves using methods well known in the art. An example of a dose-response curve is described, without limitation, in Example 4 below.

The dose of adjuvant, antigen(s) and other components in vaccine compositions should be in amounts such that the dose of antigen administered continuously or intermittently will not exceed a certain amount in consideration of the results in test animals and the individual conditions of a subject.

A specific dosage regimen will vary depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by a practitioner according to each patient's circumstances and according to standard clinical techniques.

Toxicity and therapeutic efficacy of adjuvant-containing immunogenic compositions can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects.

Kits Comprising Components for Making Vaccine Compositions

In certain embodiments, the invention provides a pharmaceutical pack or kit comprising one or more containers filled with one or more ingredients of an immunogenic formulation. In a preferred embodiment, a kit for the preparation of a pharmaceutical or vaccine composition comprises at least one antigen, adjuvant (e.g., Carbopol® or Carbopol®+DDA), an oil phase, and an aqueous phase, the kit comprising the components in different containers, and optionally instructions for admixing the components and/or for administration of the composition. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

Vaccine compositions may, if desired, be presented in a pack or dispenser device which may contain one or more unit dosage forms containing an active ingredient (i.e., an antigen and/or adjuvant). The pack may, for example, comprise metal or plastic foil, such as a blister pack. The pack or dispenser device may be accompanied by instructions for administration. Compositions formulated in a compatible pharmaceutical carrier may also be prepared, placed in an appropriate container, and labeled for vaccination against an indicated pathogen and/or condition.

Molecular Biology Definitions

In accordance with the present invention there may be employed conventional molecular biology, microbiology, and recombinant DNA techniques within the skill of the art. Such techniques are well-known and are explained fully in the literature. See, e.g., Sambrook. Fritsch and Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization [B. D. Flames & S. J. Higgins eds. (1985)]; Transcription And Translation [B. D. Flames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); and F. M. Ausubel et al. (eds.), Current Protocols in Molecular Biology, John Wiley & Sons, Inc. (1994).

A "nucleic acid molecule" (or alternatively "nucleic acid") refers to the phosphate ester polymeric form of ribonucleosides (adenosine, guanosine, uridine, or cytidine: "RNA molecules") or deoxyribonucleosides (deoxyadenosine, deoxyguanosine, deoxythymidine, or deoxycytidine: "DNA molecules"), or any phosphoester analogs thereof, such as phosphorothioates and thioesters, in either single stranded form, or a double-stranded helix. Oligonucleotides (having fewer than 100 nucleotide constituent units) or polynucleotides are included within the defined term as well as double stranded DNA-DNA, DNA-RNA, and RNA-RNA helices. This term, for instance, includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell. Generally, a DNA sequence encoding a particular protein or enzyme is "transcribed" into a corresponding sequence of mRNA. The mRNA sequence is, in turn, "translated" into the sequence of amino acids which form a protein. An "amino acid sequence" is any chain of two or more amino acids. The term "peptide" is usually used for amino acid-based polymers having fewer than 100 amino acid constituent units, whereas the term "polypeptide" is reserved for polymers having at least 100 such units. Herein, however, "polypeptide" will be the generic term.

The following examples are illustrative, but not limiting, of the method and compositions of the present invention. Other suitable modifications and adaptations of the variety of conditions and parameters normally encountered in molecular biology and chemistry which are obvious to those skilled in the art in view of the present disclosure are within the spirit and scope of the invention.

EXAMPLES

Example 1

Preparation of Control Water-In-Oil Emulsion Vaccine Formulation

Inactivated reverse genetics H5N3 avian influenza (Liu et al., *Virology* 314:580-590 (2003)) was added to sterile saline. The mixture was allowed to stir to form a homogenous mixture. Tween® 80 (7.2 mL) was added to the mixture followed by mixing to form a homogeneous aqueous mixture.

The aqueous mixture was slowly added to a mineral oil/Arlacel® 83V mixture (720 mL), such that the aqueous mixture was 40% of the total volume and the oil mixture was 60% of the total volume, to form a water-in-oil emulsion.

Example 2

Preparation of Water-In-Oil Emulsion Vaccines Containing an Adjuvant in the Aqueous Phase Water-in-oil emulsions containing an adjuvant in the aqueous phase were prepared essentially as described in Example 1. Inactivated H5N3 avian influenza and 1 of the 5 adjuvants from Table 2 was added to sterile saline to a total volume of 197 mL. The mixture was allowed to stir to form a homogenous mixture. Tween®80 (3.0 mL) was added to the mixture followed by mixing to form a homogeneous aqueous mixture.

The aqueous mixture was slowly added to a mineral oil/Arlacel® 83V mixture (300 mL), such that the aqueous mixture was 40% of the total volume and the oil mixture was 60% of the total volume, to form a water-in-oil emulsion. Thus, 5 emulsion vaccines were prepared with 5 different adjuvants.

TABLE 2

Adjuvants added to the Water-in-Oil Emulsion Vaccine Formulation

| Adjuvant | Amount |
| --- | --- |
| Al(OH)$_3$ reHydragel ® | 58.5 mL |
| Carbopol ® | 50 mL of a 2% solution |
| Carbopol ® + DDA | 33 mL of a 2% solution of Carbopol + 16.5 g DDA |
| CMC (carboxyl methylcellulose) | 1 g |
| HPMC (hydroxypropyl methylcellulose) | 1 g |

Example 3

Dosage Determination for Inoculation of Turkeys

Figure 2:
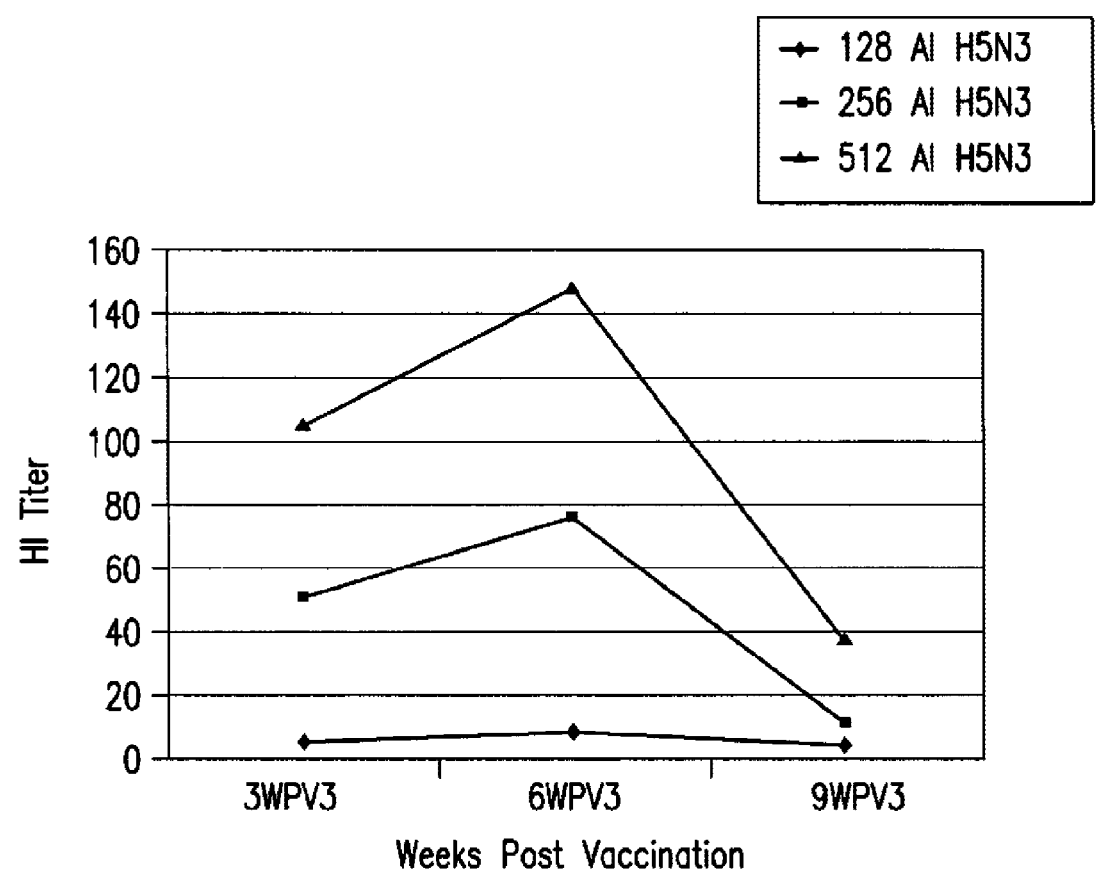
FIG. 2 shows the HI (hemaglutination inhibition) titers of the blood from turkeys inoculated with a water-in-oil emulsion vaccine formulation containing inactivated H5N3 avian influenza antigen.

Turkeys were inoculated with 128, 256, or 512 HAU (hemagglutination unit)/0.5 mL of vaccine without adjuvant, as described in Example 1. The HI (hemagglutination inhibition) titer of the blood from the inoculated turkeys was measured 3, 6, and 9 weeks after inoculation. The samples were tested with a hemagglutination inhibition (HI) assay (World Health Organization Manual on Animal Influenza Diagnosis and Surveillance, WHO/CDS/CSR/NCS/2002.5). Results are shown in FIG. 2. Although each dosage gave reasonably good serological response initially, the HI titers fell dramatically soon thereafter.

Example 4

Inoculation of Turkeys with the Water-In-Oil Emulsion Vaccine Containing an Adjuvant on the Aqueous Phase Turkeys were inoculated with vaccines containing adjuvants in the aqueous phase as described in Example 2. Ten 1-week old turkeys were vaccinated with 0.5 mL of the vaccine (256 HAU/dose). As controls, 10 turkeys were inoculated with the formulation described in Example 1 and 10 turkeys were not inoculated. Inoculated turkeys were given a second vaccination booster of 0.5 mL of vaccine (256 HAU/dose) 3 weeks after the first vaccination. Blood serum samples from the turkeys were taken at 4, 7, and 10 weeks of age and tested using the same hemaglutination inhibition assay used in Example 4. Table 3 provides a tabular description of the experimental protocol as described above.

TABLE 3

Protocol for Testing the Efficacy of Water-in-Oil Emulsion Vaccine Formulation containing an Adjuvant in the Aqueous Phase

| Age of Turkeys | Activity |
| --- | --- |
| 1 week | Bleed all turkeys. Vaccinate turkeys designated for vaccination |
| 4 weeks | Bleed all turkeys. Revaccinate turkeys designated for vaccination |
| 7 weeks | Bleed all turkeys. |
| 10 weeks | Bleed all turkeys. |

Figure 3:
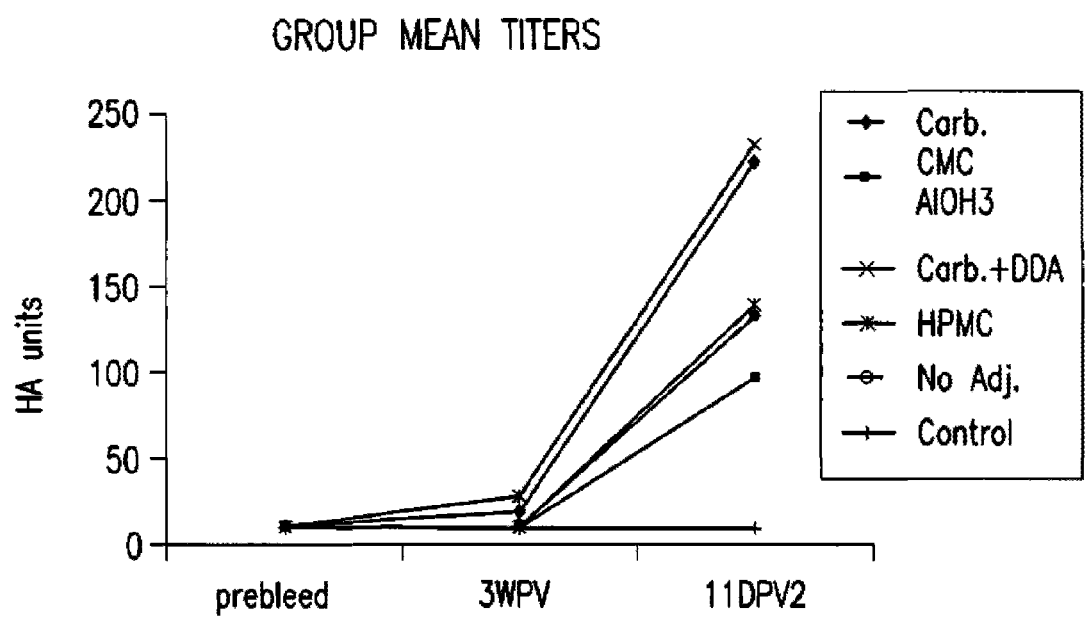
FIG. 3 shows the HI titers of the blood from control turkeys and turkeys inoculated with water-in-oil emulsion vaccines containing inactivated H5N3 avian influenza antigen and no adjuvant, Carbopol®, Carbopol®+DDA, CMC, HPMC, or Al(OH)$_3$ (reHydragel®). The HI titer levels marked as "prebleed" were from 3 non-vaccinated turkeys.

Results of control and experimental vaccinations are given in Table 4 and FIG. 3. The results demonstrate the effectiveness of vaccines comprising the Carbopol® or Carbopol®+DDA adjuvants.

TABLE 4

HI Titers for 11-week old Turkeys Inoculated with a Water-in-Oil Emulsion Vaccine Formulation with or without an Adjuvant in the Aqueous Phase

| Group | 256 HAU | Carbopol ® | Carbopol ® + DDA | vaccine w/o adjuvant | CMC | HPMC | AlOH$_3$ reHydragel |
| --- | --- | --- | --- | --- | --- | --- | --- |
| HI GMT | 120 | 222.5 | 232.5 | 133 | 97.14 | 140 | 82.5 |

(HI GMT = hemagglutination inhibition geometric mean titers)

Example 5

Enhanced Immune Response in Turkeys Obtained Using a Water-in-Oil Vaccine Composition Containing Carbopol and DDA In this example, vaccine compositions containing an avian influenza antigen in a water-in-oil emulsion, with or without Carbopol or Carbopol+DDA, were used to vaccinate turkeys, and the immune responses to the influenza antigen were evaluated.

The vaccine compositions used in this Example were prepared essentially using the general method outlined in FIG. 1. Briefly, an aqueous solution comprising avian influenza H5N9 inactivated virus was combined with an emulsifier, with or without 0.2% Carbopol or 0.2% Carbopol+0.5 g/mL DDA. The resulting mixture was slowly added to mineral oil and then subjected to emulsification/homogenization to produce either a "standard emulsion" (lacking Carbopol and DDA) or a "Carbopol emulsion" or a "Carbopol+DDA emulsion." The amount of inactivated H5N9 in the final emulsions was 512 HAU (as measured by testing on the pre-inactivated viral stock) per 0.5 mL dose.

Four groups of turkeys were used in this Example, each group consisting of 20 one-week-old commercial white turkeys. The experimental design is summarized in the following table 5:

TABLE 5

| Treatment Group | Vaccine Composition | # turkeys/route/vol. |
|---|---|---|
| 1 | Standard Emulsion | 20/IM/0.5 mL |
| 2 | Carbopol Emulsion | 20/IM/0.5 mL |
| 3 | Carbopol + DDA Emulsion | 20/IM/0.5 mL |
| 4 | Non-vaccinated Controls | 20/n.a./n.a. |

IM = intramuscular administration (turkeys were vaccinated intramuscularly in the breast).

The birds in groups 1, 2 and 3 were administered the corresponding vaccine compositions at one week of age followed by a booster vaccination at 4 weeks of age. Blood samples were collected at the time of the initial vaccination and at the time of the booster vaccination and at three-week intervals thereafter (i.e., at 7, 10, 13, 16 and 19 weeks of age). The samples were tested with a hemagglutination inhibition (HI) assay (World Health Organization Manual on Animal Influenza Diagnosis and Surveillance, WHO/CDS/CSR/NCS/2002.5). The HI assay was performed using a beta-propiolactone (BPL) inactivated H5N9 antigen stock.

The results of the HI assays (expressed in terms of geometric mean titers (GMT)) are shown in the following table 6:

TABLE 6

| | Hemagglutination Inhibition GMT** at: | | | | | |
|---|---|---|---|---|---|---|
| Treatment Group | 3 wpv1 | 3 wpv2 | 6 wpv2 | 9 wpv2 | 12 wpv2 | 15 wpv2 |
| 1 (standard emulsion) | 26 | 111 | 74 | 26 | 18 | 25 |
| 2 (Carbopol) | 36 | 453 | 333 | 187 | 118 | 83 |
| 3 (Carbopol + DDA) | 36 | 67 | 51 | 28 | 29 | 33 |
| 4 (nonvaccinated control) | 5 | 5 | 5 | 5 | 5 | 5 | wpv1 = weeks post vaccination 1;
wpv2 = weeks post vaccination 2
**For calculation of GMT, an individual bird titer that was negative at 1:10 (the lowest dilution tested) was assigned a value of 5.

Turkeys vaccinated with H5N9 antigen+Carbopol emulsion (Group 2) or with H5N9 antigen+Carbopol+DDA emulsion (Group 3) exhibited higher HI GMTs as compared to birds vaccinated with H5N9 antigen only standard emulsion (Group 1). Further, the higher level of serologic response in turkeys administered the Carbopol inclusive emulsion lasted for the duration of the study to 15 weeks after booster vaccination (turkeys at 19 weeks of age).

In this Example, a general enhancement of serologic response was observed to avian influenza in turkeys administered a water-in-oil vaccine emulsion inclusive of Carbopol or Carbopol+DDA in the aqueous phase. This enhancement occurred with a conventional low-pathogenic H5N9 isolate, similar to the results observed utilizing the reverse genetics origin low-pathogenic H5N3 isolate (Example 4). Therefore, the enhanced immune response can be attributed to the adjuvant and is apparently applicable to a variety of antigens.

Example 6

Enhanced Immune Response in Ducks Obtained Using a Water-in-Oil Vaccine Composition Containing Carbopol In this example, vaccine compositions containing an avian influenza antigen in a water-in-oil emulsion, with or without Carbopol in the aqueous phase, were used to vaccinate four different breeds of ducks, and the immune responses to the influenza antigen were evaluated.

The vaccine compositions used in this Example were prepared essentially using the general method outlined in FIG. 1. Briefly, an aqueous solution comprising reverse genetics avian influenza H5N3 inactivated virus ("rg-H5N3," see Example 1) was combined with an emulsifier, with or without 0.2% Carbopol. The resulting mixture was slowly added to mineral oil and then subjected to emulsification/homogenization to produce either a "standard emulsion" (lacking Carbopol) or a "Carbopol emulsion" (containing 0.2% Carbopol in the aqueous phase). The amount of rg-H5N3 in the final emulsions was 256 HAU per 0.5 mL dose.

In this Example, four different breeds of duck were used: Pekin, Mallard, Khaki Campbell and Golden Hybrid 300. Each breed of duck was subdivided into three different treatment groups as shown in the following table 7:

TABLE 7

| Breed | Treatment Group | Vaccine Composition | Number of Ducks per Treatment Group |
|---|---|---|---|
| Pekin | 1 | Standard Emulsion | 20 |
| | 2 | Carbopol Emulsion | 20 |
| | 3 | Nonvaccinated Controls | 10 |
| Mallard | 1 | Standard Emulsion | 20 |
| | 2 | Carbopol Emulsion | 20 |
| | 3 | Nonvaccinated Controls | 10 |

TABLE 7-continued

| Breed | Treatment Group | Vaccine Composition | Number of Ducks per Treatment Group |
|---|---|---|---|
| Khaki Campbell | 1 | Standard Emulsion | 20 |
|  | 2 | Carbopol Emulsion | 20 |
|  | 3 | Nonvaccinated Controls | 10 |
| Golden Hybrid 300 | 1 | Standard Emulsion | 20 |
|  | 2 | Carbopol Emulsion | 20 |
|  | 3 | Nonvaccinated Controls | 10 |

The ducks in treatment groups 1 and 2 were vaccinated subcutaneously in the back of the neck with 0.2 mL total volume of the corresponding emulsion vaccine composition at day of age ("primary vaccination"). At three weeks of age, the ducks were boosted with 0.5 mL of the same vaccine subcutaneously in the back of the neck.

Blood samples were collected at the time of the primary vaccination and at three-week intervals thereafter, i.e., at 3 weeks after the primary vaccination ("3 WPV1") and at 3, 6, 9 and 12 weeks after the booster vaccination ("3 WPV2," "6 WPV2," "9 WPV2," and "12 WPV2."). The samples were tested with a hemagglutination inhibition (HI) assay (World Health Organization Manual on Animal Influenza Diagnosis and Surveillance, WHO/CDS/CSR/NCS/2002.5). The HI assay was performed using a beta-propiolactone (BPL) inactivated H5N3 antigen stock.

Sera collected from representative ducks of each breed at day-of-age (prior to vaccination) was free of HI detectable antibody to avian influenza. (Data not shown.) The results of the HI assays (expressed in terms of geometric mean titers (GMT)) for the remaining time points are shown in the following table 8:

TABLE 8

|  |  | Hemagglutination Inhibition GMT** at: | | | | |
|---|---|---|---|---|---|---|
| Breed | Treatment Group | 3 WPV1 | 3 WPV2 | 6 WPV2 | 9 WPV2 | 12 WPV2 |
| Pekin | 1 (standard emulsion) | 9 | 14 | 12 | 7 | 6 |
|  | 2 (Carbopol) | 17 | 180 | 80 | 52 | 50 |
|  | 3 (nonvaccinated) | 5 | 5 | 5 | 5 | 5 |
| Mallard | 1 (standard emulsion) | 8 | 90 | 36 | 20 | 24 |
|  | 2 (Carbopol) | 34 | 170 | 120 | 97 | 67 |
|  | 3 (nonvaccinated) | 5 | 5 | 5 | 5 | 5 |
| Khaki Campbell | 1 (standard emulsion) | 11 | 115 | 42 | 16 | 16 |
|  | 2 (Carbopol) | 29 | 238 | 138 | 76 | 57 |
|  | 3 (nonvaccinated) | 5 | 5 | 5 | 5 | 5 |
| Golden Hybrid 300† | 1 (standard emulsion) | 17 | 126 | 83 | 72 | 75 |
|  | 2 (Carbopol) | 28 | 107 | 50 | 38 | 25 |
|  | 3 (nonvaccinated) | 5 | 5 | 5 | 5 | 5 |

WPV1 = weeks post vaccination 1; WPV2 = weeks post vaccination 2.
†It is suspected that the 'standard emulsion' results and 'Carbopol' results for Golden Hybrid 300 ducks were inadvertently switched at some point during the experiment.
**For calculation of GMT, an individual bird titer that was negative at 1:10 (the lowest dilution tested) was assigned a value of 5.

The results presented above show that water-in-oil vaccine compositions formulated with Carbopol in the aqueous phase produced significantly greater immune responses in most breeds of duck tested as compared to water-in-oil vaccine compositions formulated without Carbopol in the aqueous phase. These results further confirm that water-in-oil vaccine compositions comprising an acrylic polymer (e.g., Carbopol) in the aqueous phase provide superior immune responses as compared to conventional water-in-oil vaccine compositions.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A vaccine composition comprising an antigen component and an adjuvant component, wherein the adjuvant component comprises an oil-in-water emulsion, wherein further an aqueous phase of said oil-in-water emulsion comprises dimethyl dioctadecyl ammonium bromide (DDA) and an alkyl-polyacrylic acid (alkyl-PAA).

2. The vaccine composition of claim 1, wherein said oil comprises at least one oil selected from the group consisting of a mineral oil, a terpene oil, soybean oil, olive oil, and a propylene glycol derivative.

3. The vaccine composition of claim 1, wherein the adjuvant component further comprises at least one of CpG DNA, lipopolysaccharides, and monophosphoryl lipid A.

4. The vaccine composition of claim 3, wherein the adjuvant component comprises CpG DNA and monophosphoryl lipid A.

5. The vaccine composition of claim 1, wherein the composition further comprises one or more emulsifiers.

6. The vaccine composition of claim 1, wherein the antigen is a poultry vaccine antigen.

* * * * *